United States Patent
Knopp et al.

(10) Patent No.: US 9,044,160 B2
(45) Date of Patent: Jun. 2, 2015

(54) APPARATUS AND METHOD FOR GENERATING AND MOVING A MAGNETIC FIELD HAVING A FIELD FREE LINE

(75) Inventors: Tobias Knopp, Lubeck (DE); Timo Frederik Sattel, Lubeck (DE); Sven Biederer, Luebeck (DE); Thorsten Manuel Buzug, Grob Sarau (DE)

(73) Assignee: Koninklijke Philips N.V., Eindhoven (NL)

(*) Notice: Subject to any disclaimer, the term of this patent is extended or adjusted under 35 U.S.C. 154(b) by 622 days.

(21) Appl. No.: 13/388,302

(22) PCT Filed: Aug. 19, 2010

(86) PCT No.: PCT/IB2010/053749
§ 371 (c)(1),
(2), (4) Date: Feb. 1, 2012

(87) PCT Pub. No.: WO2011/021165
PCT Pub. Date: Feb. 24, 2011

(65) Prior Publication Data
US 2012/0126808 A1   May 24, 2012

(30) Foreign Application Priority Data
Aug. 21, 2009 (EP) .................................. 09168383

(51) Int. Cl.
*G01V 3/00* (2006.01)
*A61B 5/055* (2006.01)
(Continued)

(52) U.S. Cl.
CPC .............. *A61B 5/055* (2013.01); *G01R 33/445* (2013.01); *A61B 5/0515* (2013.01)

(58) Field of Classification Search
CPC .................................................. G01R 33/445

USPC .................................. 324/319, 318, 322, 300
See application file for complete search history.

(56) References Cited

U.S. PATENT DOCUMENTS 7,994,786 B2 *  8/2011  Weaver et al. ................ 324/318
8,350,566 B2 *  1/2013  Ohyu et al. ................... 324/300
(Continued)

FOREIGN PATENT DOCUMENTS

DE    10151778 A1    8/2003
EP    1304542 A2    10/2002
(Continued)

OTHER PUBLICATIONS

Gleich et al. "Tomographic imaging using the nonlinear response of magnetic particles". Nature, Nature Publishing Group, London, GB, vol. 435, No. 7046, Jun. 30, 2005, pp. 1214-1217.
(Continued)

*Primary Examiner* — Louis Arana

(57) ABSTRACT

The present invention relates to an apparatus and a method for generating and changing a magnetic field in a field of view (28), said magnetic field having a, in particular ball-shaped or line-shaped, first sub-zone (62) having a low magnetic field strength and a second sub-zone (64) having a higher magnetic field strength. The proposed apparatus comprises at least three pairs of first coils (136a-136d), wherein the coils are arranged along a ring around the field of view and wherein the two coils of each pair are opposingly arranged on opposite sides of the field of view, at least one pair of second coils (116) opposingly arranged on opposite sides of the field of view at the open sides of said ring, generator means (110, 130) for generating current signals for provision to said first and second coils for generating the desired magnetic fields by said first and second coils, and control means (150) for controlling said generator means.

14 Claims, 10 Drawing Sheets

(51) Int. Cl.
 *G01R 33/44* (2006.01)
 *A61B 5/05* (2006.01)

(56) References Cited

U.S. PATENT DOCUMENTS 8,355,771 B2 1/2013 Gleich
8,666,473 B2 * 3/2014 Gleich .................. 600/409

FOREIGN PATENT DOCUMENTS

| WO | 2004091386 | A2 | 10/2004 |
| WO | 2004091390 | A2 | 10/2004 |
| WO | 2004091394 | A2 | 10/2004 |
| WO | 2004091395 | A2 | 10/2004 |
| WO | 2004091396 | A2 | 10/2004 |
| WO | 2004091397 | A2 | 10/2004 |
| WO | 2004091398 | A2 | 10/2004 |
| WO | 2004091408 | A2 | 10/2004 |

OTHER PUBLICATIONS

Weizenecker et al. "Magnetic particle imaging using a field free line". Journal of Physics D. Applied Physics, IOP Publishing, Bristol, GB. vol. 41, No. 10, May 21, 2008, p. 105009.

* cited by examiner

APPARATUS AND METHOD FOR GENERATING AND MOVING A MAGNETIC FIELD HAVING A FIELD FREE LINE

FIELD OF THE INVENTION

The present invention relates to an apparatus and a method for generating and changing a magnetic field in a field of view, said magnetic field having a, in particular ball-shaped or line-shaped, first sub-zone having a low magnetic field strength and a second sub-zone having a higher magnetic field strength.

Further, the present invention relates to a computer program for implementing said method on a computer and for controlling such an apparatus.

Still further, the present relates to a magnetic particle imaging apparatus for influencing and/or detecting magnetic particles in a field of view.

BACKGROUND OF THE INVENTION

Magnetic fields play an important role in a wide range of applications. They are used for instance in electric motors, dynamos and for signal transmission of radio or television. Furthermore, magnetic fields are used for medical diagnosis, where the most prominent example is magnetic resonance imaging (MRI). In each of these applications, the magnetic field is tailored to fulfill certain needs. For instance, in MRI, the formation of two field configurations is required: A spatially homogeneous and a linearly increasing gradient field. These special fields can be generated by electromagnetic coils, whereas the coil geometry and the applied current determine the field characteristics. For these simple field configurations, the optimal coil topology is well known. A homogeneous magnetic field is generated by a Helmholtz coil pair consisting of two identical coils that are placed symmetrically along a common axis, and separated by distance R equal to the coil radius. Each coil carries equal current owing in same direction. Similarly, a gradient field is generated by a Maxwell coil pair, which has the same topology but current owing in opposing direction and a larger coil distance of $R\sqrt{3}$.

Magnetic Particle Imaging (MPI) is an emerging medical imaging modality. The first versions of MPI were two-dimensional in that they produced two-dimensional images. Future versions will be three-dimensional (3D). A time-dependent, or 4D, image of a non-static object can be created by combining a temporal sequence of 3D images to a movie, provided the object does not significantly change during the data acquisition for a single 3D image.

MPI is a reconstructive imaging method, like Computed Tomography (CT) or Magnetic Resonance Imaging (MRI). Accordingly, an MP image of an object's volume of interest is generated in two steps. The first step, referred to as data acquisition, is performed using an MPI scanner. The MPI scanner has means to generate a static magnetic gradient field, called "selection field", which has a single field free point (FFP) at the isocenter of the scanner. In addition, the scanner has means to generate a time-dependent, spatially nearly homogeneous magnetic field. Actually, this field is obtained by superposing a rapidly changing field with a small amplitude, called "drive field", and a slowly varying field with a large amplitude, called "focus field". By adding the time-dependent drive and focus fields to the static selection field, the FFP may be moved along a predetermined FFP trajectory throughout a volume of scanning surrounding the isocenter. The scanner also has an arrangement of one or more, e.g. three, receive coils and can record any voltages induced in these coils. For the data acquisition, the object to be imaged is placed in the scanner such that the object's volume of interest is enclosed by the scanner's field of view, which is a subset of the volume of scanning.

The object must contain magnetic nanoparticles; if the object is an animal or a patient, a contrast agent containing such particles is administered to the animal or patient prior to the scan. During the data acquisition, the MPI scanner steers the FFP along a deliberately chosen trajectory that traces out the volume of scanning, or at least the field of view. The magnetic nanoparticles within the object experience a changing magnetic field and respond by changing their magnetization. The changing magnetization of the nanoparticles induces a time dependent voltage in each of the receive coils. This voltage is sampled in a receiver associated with the receive coil. The samples output by the receivers are recorded and constitute the acquired data. The parameters that control the details of the data acquisition make up the scan protocol.

In the second step of the image generation, referred to as image reconstruction, the image is computed, or reconstructed, from the data acquired in the first step. The image is a discrete 3D array of data that represents a sampled approximation to the position-dependent concentration of the magnetic nanoparticles in the field of view. The reconstruction is generally performed by a computer, which executes a suitable computer program. Computer and computer program realize a reconstruction algorithm. The reconstruction algorithm is based on a mathematical model of the data acquisition. As with all reconstructive imaging methods, this model is an integral operator that acts on the acquired data; the reconstruction algorithm tries to undo, to the extent possible, the action of the model.

Such an MPI apparatus and method have the advantage that they can be used to examine arbitrary examination objects—e.g. human bodies—in a non-destructive manner and without causing any damage and with a high spatial resolution, both close to the surface and remote from the surface of the examination object. Such an arrangement and method are generally known and are first described in DE 101 51 778 A1 and in Gleich, B. and Weizenecker, J. (2005), "Tomographic imaging using the nonlinear response of magnetic particles" in nature, vol. 435, pp. 1214-1217. The arrangement and method for magnetic particle imaging (MPI) described in that publication take advantage of the non-linear magnetization curve of small magnetic particles.

In the paper Weizenecker J. et al., "Magnetic particle imaging using a field free line", J. Phys. D: Appl. Phys. 41 (2008) 105009, a simulation study on the use of a field free line (FFL) in magnetic particle imaging is presented. Further, a schematic setup of the simulated scanner geometry and the path of the FFL are described. The setup comprises a ring of 32 small coils (selection field coils) producing the rotating FFL. Two pairs of larger loops (drive field coils) move this FFL over the field of view. The diameter of the selection field coil ring is 1 m. Superimposing the selection field and the drive field, the FFL moves along the drive field vector, which over time has the form of a rosette, provided that the orientation of the FFL is always perpendicular to the drive field vector. Hence, the FFL scans back and forth while rotating slowly. This setup has, however, significantly higher power losses than the above described MPI apparatus exploiting the use and movement of a FFP and, hence, might not be realizable.

SUMMARY OF THE INVENTION

It is an object of the present invention to provide an apparatus and a method for generating and changing a desired magnetic field in a field of view, in particular for generating and moving a field free line with less power losses than the setup described in the above mentioned paper Weizenecker J. et al., "Magnetic particle imaging using a field free line".

It is a further object of the present invention to provide a computer program for implementing said method on a computer and for controlling such an apparatus.

It is a further object of the present invention to provide a magnetic particle imaging apparatus for influencing and/or detecting magnetic particles in a field of view.

In a first aspect of the present invention an apparatus for generating and changing a magnetic field in a field of view, said magnetic field having a, in particular ball-shaped or line-shaped, first sub-zone having a low magnetic field strength and a second sub-zone having a higher magnetic field strength, which apparatus comprises:

at least three pairs of first coils, wherein the coils are arranged along a ring around the field of view at equal or unequal distances from the center of the field of view, and wherein the two coils of each pair are opposingly arranged on opposite sides of the field of view, at least one pair of second coils opposingly arranged on opposite sides of the field of view at the open sides of said ring, generator means for generating current signals for provision to said first and second coils for generating the desired magnetic fields by said first and second coils, and control means for controlling said generator means to generate i) selection field current signals for provision to said first coils so that the at least three pairs of first coils generate a gradient magnetic selection field having a pattern in space of its magnetic field strength such that a, in particular ball-shaped or line-shaped, first sub-zone having a low magnetic field strength and a second sub-zone having a higher magnetic field strength are formed in the field of view and ii) drive field current signals for provision to said second coils and to two pairs of first coils so that the at least one pair of second coils and said two pairs of first coils generate a homogeneous magnetic drive field for changing the position in space of the two sub-zones in the field of view.

In a further aspect of the present invention a corresponding method is presented as well as computer program for implementing said method.

Finally, in a still further aspect a magnetic particle imaging apparatus for influencing and/or detecting magnetic particles in a field of view, which apparatus comprises an apparatus for generating and changing a magnetic field in the field of view according to the present invention.

Preferred embodiments of the invention are defined in the dependent claims. It shall be understood that the claimed method and the claimed computer program have similar and/or identical preferred embodiments as the claimed apparatus and as defined in the dependent claims.

The present invention is mainly directed to generating and moving a field-free line (FFL), i.e. the line-shaped first sub-zone, which is required to be arbitrarily rotated by only changing the applied currents while keeping the coil geometry static in space. Perpendicular to the FFL, the field is supposed to increase linearly with a high gradient. It has been found by the inventors of the present invention that an FFL can be generated by only three rotated Maxwell coil pairs using appropriate currents. Furthermore, the FFL can be translated by additional Helmholtz coil pairs.

To improve sensitivity compared to the above described MPI apparatus for generating and using a FFP (also called FFP scanner in the following), the FFL is conjectured to increase SNR by one order of magnitude compared to FFP imaging. To this end, an encoding scheme is used, much like it is applied in computed tomography. More precisely, FFL signal encoding requires a slowly rotating FFL, which is rapidly moved back and forth. However, no proof was given, that the setup for generating a FFL presented in the above mentioned paper by Weizenecker consisting of 32 electromagnetic coils actually generates an FFL. Moreover, the suggested scanner requires about 1000 times the power of a conventional FFP scanner. According to the present invention a new FFL coil assembly is presented requiring roughly the same power as an FFP scanner of equal size and gradient performance.

According to a preferred embodiment the control means are adapted for controlling said generator means to generate selection field current signals also for provision to said second coils for contributing to the generation of the magnetic selection field. In this way the quality of the desired magnetic selection field can be improved.

Generally three pairs of first coils are sufficient, but in a further embodiment at least a fourth pair of first coils is provided, wherein all first coils are arranged along a ring around the field of view. Preferably, four pairs are provided in which case the two pairs contributing to the generation of the magnetic drive can be arranged perpendicularly to each other, which generally is not possible with 3 pairs of in total 6 coils arranged at equispaced angles around the ring.

Preferably, said first coils are arranged along said ring without overlapping each other, at equispaced angles and/or at equal distance from the center of the field of view. If the distances from the center or the angular positions are not equal the currents provided to the individual coils have to be adapted accordingly. If the first coils are placed at equispaced angles and at equal distances from the center the control of the currents provided to the first coils is less complex and the obtained magnetic fields are easier to predict.

According to another embodiment said generator means comprises a selection field current signal generator unit for generating individual selection field current signals for each of said first coils in the form of a sinusoidal function depending on the angular position of the respective first coil along the ring and the desired direction of a line-shaped first sub-zone. Preferably, said selection field current signal generator unit is adapted for generating said individual selection field current signals $I_l$ for each of said first coils l in the form of $I_l = g_l(\gamma - \cos(2\phi_l - 2\alpha))$, wherein $\phi_l$ is the angular position of the respective first coil l along the ring, $\alpha$ determines the desired direction of the line-shaped first sub-zone in the field of view and $g_l$ and $\gamma$ are predetermined constants.

The parameter $g_l$ determine the width of the line-shaped first sub-zone. Generally, a gradient strength, e.g. of 2 T/m, is desired in a direction perpendicular to the field free line. To define here more exactly the currents that are provided the coils is impossible since the currents are dependent also on the number of windings, the absolute distances of the coils etc.

In practice the magnetic fields are often simulated, and the right currents are found by such simulations. Hence, the parameter $g_l$ is adapted so that the desired gradient field strength perpendicularly to the field free line is achieved. The parameter $g_l$ is generally selected for each individual coil l, i.e. depends on l, if the distances of the coils are different for different pairs of coils. Preferably, the parameters $g_l$ are selected such that the coils of a coil pair, at the same current signal $I_l = g_l$, generate the same gradient field, but rotated by $\phi_l$.

The parameter γ generally has a fixed, predetermined value, e.g. 3/2 at which a FFL is best obtained.

According to a further embodiment said selection field current signal generator unit is adapted for generating said individual selection field current signals $I_l$ for each of said first coils l in the form of $I_l = g_l \cos(2\phi_l - 2\alpha)$, wherein $\phi_l$ is the angular position of the respective first coil l along the ring, α determines the desired direction of a line-shaped first sub-zone in the field of view and $g_l$ is a predetermined constant, and said individual selection field current signals $I_m$ for each of said second coils m for generating a gradient magnetic field in a direction perpendicular to the ring of said first coils.

In this embodiment the generation of the selection field is further improved. Preferably, for the individual selection field current signals $I_m$ for each of said second coils m holds $I_m = g_m$ wherein for the parameter $g_m$ generally the same holds as explained above for the parameter $g_l$. In this way the individual selection field current signals $I_m$ are static and independent from the angle of the FFL within the field of view.

Preferably, said second coils are controlled such that they generate a gradient magnetic field which is ¾*L times the gradient magnetic field generated by the first coils, but in a direction perpendicular to the plane of the ring. Here, L is the number of coils pairs of first coils. With this embodiment a good FFL is obtained.

In a still further embodiment said selection field current signal generator unit is adapted for generating said individual selection field current signals such that the parameter α determining the desired direction of the line-shaped first sub-zone is continuously varied over time t, in particular according to α=2πft, wherein f is the frequency by which the line-shaped first subzone is rotating. In this way the field free line can be rotated by the frequency f and can thus be moved along a predetermined trajectory, e.g. to sample the whole field of view with a desired resolution, for instance when applied in an MPI apparatus.

It is further advantageous if said generator means comprises a drive field current signal generator unit for generating individual drive field current signals for each of said second coils and said two pairs of first coils, to which said drive field current signals are provided, causing said first and second coils to generate homogeneous magnet fields having a magnetic field vector pointing into the direction of desired movement of the line-shaped first sub-zone, in particular pointing into the direction perpendicular to the line-shaped first sub-zone. In this way the field free line can be easily moved in the desired direction. The relationship of the currents provided to the individual coils again depends on the distance, number of windings and sizes of the coils etc.

A still further embodiment comprises three pairs of second coils opposingly arranged on various opposite sides of the field of view. In this way, it is possible to use only these second coils for generating the drive fields and use the first coils only for generating the selection field. Further, it is easier to freely move the first sub-zone.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Before the details of the present invention shall be explained, basics of magnetic particle imaging shall be explained in detail with reference to FIGS. 1 to 3. In particular, two embodiments of an MPI scanner for medical diagnostics will be described. An informal description of the data acquisition is also given. The similarities and differences between the two embodiments will be pointed out.

Figure 1:
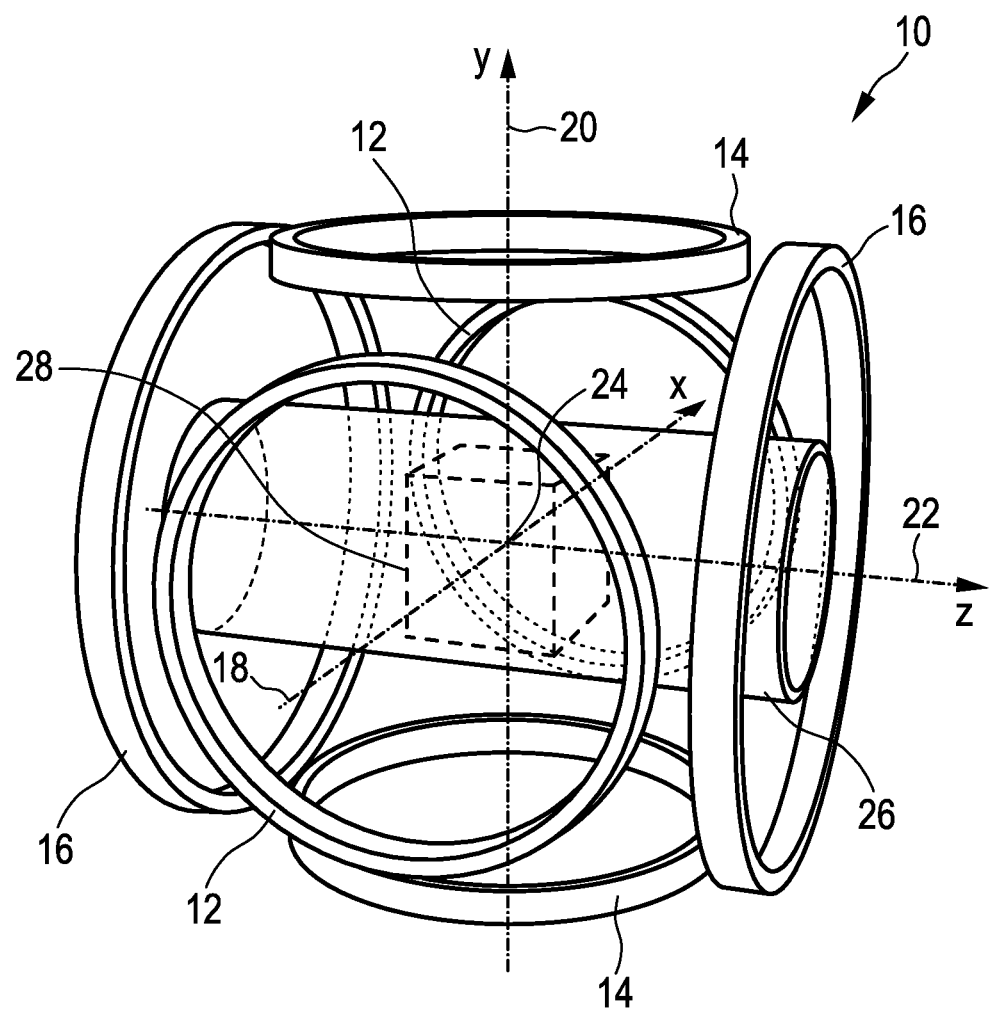
FIG. 1 shows a first embodiment of an MPI apparatus.

The first embodiment 10 of an MPI scanner shown in FIG. 1 has three prominent pairs 12, 14, 16 of coaxial parallel circular coils, each pair being arranged as illustrated in FIG. 1. These coil pairs 12, 14, 16 serve to generate the selection field as well as the drive and focus fields. The axes 18, 20, 22 of the three coil pairs 12, 14, 16 are mutually orthogonal and meet in a single point, designated the isocenter 24 of the MPI scanner 10. In addition, these axes 18, 20, 22 serve as the axes of a 3D Cartesian x-y-z coordinate system attached to the isocenter 24. The vertical axis 20 is nominated the y-axis, so that the x and z-axes are horizontal. The coil pairs 12, 14, 16 are also named after their axes. For example, the y-coil pair 14 is formed by the coils at the top and the bottom of the scanner. Moreover, the coil with the positive (negative) y-coordinate is called the y⁺-coil (y⁻-coil), and similarly for the remaining coils.

The scanner 10 can be set to direct a predetermined, time dependent electric current through each of these coils 12, 14, 16, and in either direction. If the current flows clockwise around a coil when seen along this coil's axis, it will be taken as positive, otherwise as negative. To generate the static selection field, a constant positive current $I^S$ is made to flow through the z⁺-coil, and the current $-I^S$ is made to flow through the z⁻-coil. The z-coil pair 16 then acts as an antiparallel circular coil pair.

Figure 2:
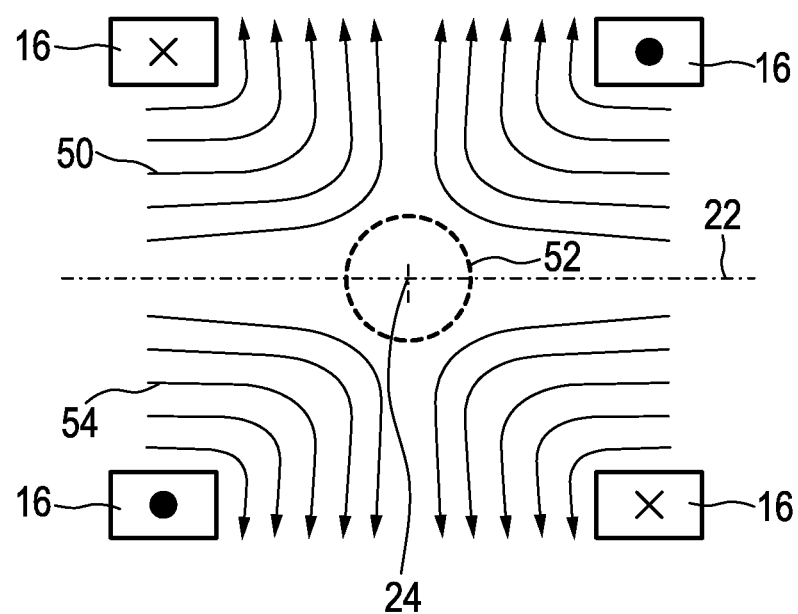
FIG. 2 shows an example of the selection field pattern produced by an apparatus as shown in FIG. 1.

The magnetic selection field which is generally a gradient magnetic field is represented in FIG. 2 by the field lines 50. It has a substantially constant gradient in the direction of the (e.g. horizontal) z-axis 22 of the z-coil pair 16 generating the selection field and reaches the value zero in the isocenter 24 on this axis 22. Starting from this field-free point (not individually shown in FIG. 2), the field strength of the magnetic selection field 50 increases in all three spatial directions as the distance increases from the field-free point. In a first sub-zone or region 52 which is denoted by a dashed line around the isocenter 24 the field strength is so small that the magnetization of particles present in that first sub-zone 52 is not saturated, whereas the magnetization of particles present in a second sub-zone 54 (outside the region 52) is in a state of saturation. The field-free point or first sub-zone 52 of the scanner's field of view 28 is preferably a spatially coherent area; it may also be a punctiform area, a line or a flat area. In the second sub-zone 54 (i.e. in the residual part of the scanner's field of view 28 outside of the first sub-zone 52) the magnetic field strength of the selection field is sufficiently strong to keep the magnetic particles in a state of saturation.

By changing the position of the two sub-zones 52, 54 within the field of view 28, the (overall) magnetization in the field of view 28 changes. By measuring the magnetization in the field of view 28 or physical parameters influenced by the magnetization, information about the spatial distribution of the magnetic particles in the field of view 28 can be obtained. In order to change the relative spatial position of the two sub-zones 52, 54 in the field of view 28, further magnetic fields, i.e. the magnetic drive field, and, if applicable, the magnetic focus field, are superposed to the selection field 50 in the field of view 28 or at least in a part of the field of view 28.

To generate the drive field, a time dependent current $I^D_1$ is made to flow through both x-coils 12, a time dependent current $I^D_2$ through both y-coils 14, and a time dependent current $I^D_3$ through both z-coils 16. Thus, each of the three coil pairs acts as a parallel circular coil pair. Similarly, to generate the focus field, a time dependent current $I^F_1$ is made to flow through both x-coils 12, a current $I^F_2$ through both y-coils 14, and a current $I^F_3$ through both z-coils 16.

It should be noted that the z-coil pair 16 is special: It generates not only its share of the drive and focus fields, but also the selection field. The current flowing through the z$^\pm$-coil is $I^D_3+I^F_3+I^S$. The current flowing through the remaining two coil pairs 12, 14 is $I^D_k+I^F_k$, k=1, 2. Because of their geometry and symmetry, the three coil pairs 12, 14, 16 are well decoupled. This is wanted.

Being generated by an anti-parallel circular coil pair, the selection field is rotationally symmetric about the z-axis, and its z-component is nearly linear in z and independent of x and y in a sizeable volume around the isocenter 24. In particular, the selection field has a single field free point (FFP) at the isocenter. In contrast, the contributions to the drive and focus fields, which are generated by parallel circular coil pairs, are spatially nearly homogeneous in a sizeable volume around the isocenter 24 and parallel to the axis of the respective coil pair. The drive and focus fields jointly generated by all three parallel circular coil pairs are spatially nearly homogeneous and can be given any direction and strength, up to some maximum strength. The drive and focus fields are also time dependent. The difference between the focus field and the drive field is that the focus field varies slowly in time and has a large amplitude while the drive field varies rapidly and has a small amplitude. There are physical and biomedical reasons to treat these fields differently. A rapidly varying field with a large amplitude would be difficult to generate and hazardous to the patient.

The embodiment 10 of the MPI scanner has at least one further pair, preferably three further pairs, of parallel circular coils, again oriented along the x-, y-, and z-axes. These coil pairs, which are not shown in FIG. 1, serve as receive coils. As with the coil pairs 12, 14, 16 for the drive and focus fields, the magnetic field generated by a constant current flowing through one of these receive coil pairs is spatially nearly homogeneous within the field of view and parallel to the axis of the respective coil pair. The receive coils are supposed to be well decoupled. The time dependent voltage induced in a receive coil is amplified and sampled by a receiver attached to this coil. More precisely, to cope with the enormous dynamic range of this signal, the receiver samples the difference between the received signal and a reference signal. The transfer function of the receiver is non-zero from DC up to the point where the expected signal level drops below the noise level.

The embodiment 10 of the MPI scanner shown in FIG. 1 has a cylindrical bore 26 along the z-axis 22, i.e. along the axis of the selection field. All coils are placed outside this bore 26. For the data acquisition, the patient (or object) to be imaged (or treated) is placed in the bore 26 such that the patient's volume of interest—that volume of the patient (or object) that shall be imaged (or treated)—is enclosed by the scanner's field of view 28—that volume of the scanner whose contents the scanner can image. The patient (or object) is, for instance, placed on a patient table. The field of view 28 is a geometrically simple, isocentric volume in the interior of the bore 26, such as a cube, a ball, or a cylinder. A cubical field of view 28 is illustrated in FIG. 1.

The size of the first sub-zone 52 is dependent on the one hand on the strength of the gradient of the magnetic selection field and on the other hand on the field strength of the magnetic field required for saturation. For a sufficient saturation of the magnetic particles at a magnetic field strength of 80 A/m and a gradient (in a given space direction) of the field strength of the magnetic selection field amounting to $50\times10^3$ A/m$^2$, the first sub-zone 52 in which the magnetization of the particles is not saturated has dimensions of about 1 mm (in the given space direction).

The patient's volume of interest is supposed to contain magnetic nanoparticles. Especially prior to a therapeutic and/or diagnostic treatment of, for example, a tumor, the magnetic particles are positioned in the volume of interest, e.g. by means of a liquid comprising the magnetic particles which is injected into the body of the patient (object) or otherwise administered, e.g. orally, to the patient.

An embodiment of magnetic particles comprises, for example, a spherical substrate, for example, of glass which is provided with a soft-magnetic layer which has a thickness of, for example, 5 nm and consists, for example, of an iron-nickel alloy (for example, Permalloy). This layer may be covered, for example, by means of a coating layer which protects the particle against chemically and/or physically aggressive environments, e.g. acids. The magnetic field strength of the magnetic selection field 50 required for the saturation of the magnetization of such particles is dependent on various parameters, e.g. the diameter of the particles, the used magnetic material for the magnetic layer and other parameters.

In the case of e.g. a diameter of 10 μm, a magnetic field of approximately 800 A/m (corresponding approximately to a flux density of 1 mT) is then required, whereas in the case of a diameter of 100 μm a magnetic field of 80 A/m suffices. Even smaller values are obtained when a coating of a material having a lower saturation magnetization is chosen or when the thickness of the layer is reduced. Magnetic particles that can generally be used are available on the market under the trade name Resovist.

For further details of the generally usable magnetic particles and particle compositions, the corresponding parts of EP 1304542, WO 2004/091386, WO 2004/091390, WO 2004/091394, WO 2004/091395, WO 2004/091396, WO 2004/091397, WO 2004/091398, WO 2004/091408 are herewith referred to, which are herein incorporated by reference. In these documents more details of the MPI method in general can be found as well.

The data acquisition starts at time $t_s$ and ends at time $t_e$. During the data acquisition, the x-, y-, and z-coil pairs 12, 14, 16 generate a position- and time dependent magnetic field, the applied field. This is achieved by directing suitable currents through the coils. In effect, the drive and focus fields push the selection field around such that the FFP moves along a preselected FFP trajectory that traces out the volume of scanning—a superset of the field of view. The applied field orientates the magnetic nanoparticles in the patient. As the applied field changes, the resulting magnetization changes too, though it responds nonlinearly to the applied field. The sum of the changing applied field and the changing magnetization induces a time dependent voltage $V_k$ across the terminals of receive coil pair along the $x_k$-axis. The associated receiver converts this voltage to a signal $S_k(t)$, which it samples and outputs.

It is advantageous to receive or to detect signals from the magnetic particles located in the first sub-zone 52 in another frequency band (shifted to higher frequencies) than the frequency band of the magnetic drive field variations. This is possible because frequency components of higher harmonics of the magnetic drive field frequency occur due to a change in magnetization of the magnetic particles in the scanner's field of view 28 as a result of the non-linearity of the magnetization characteristics.

Figure 3:
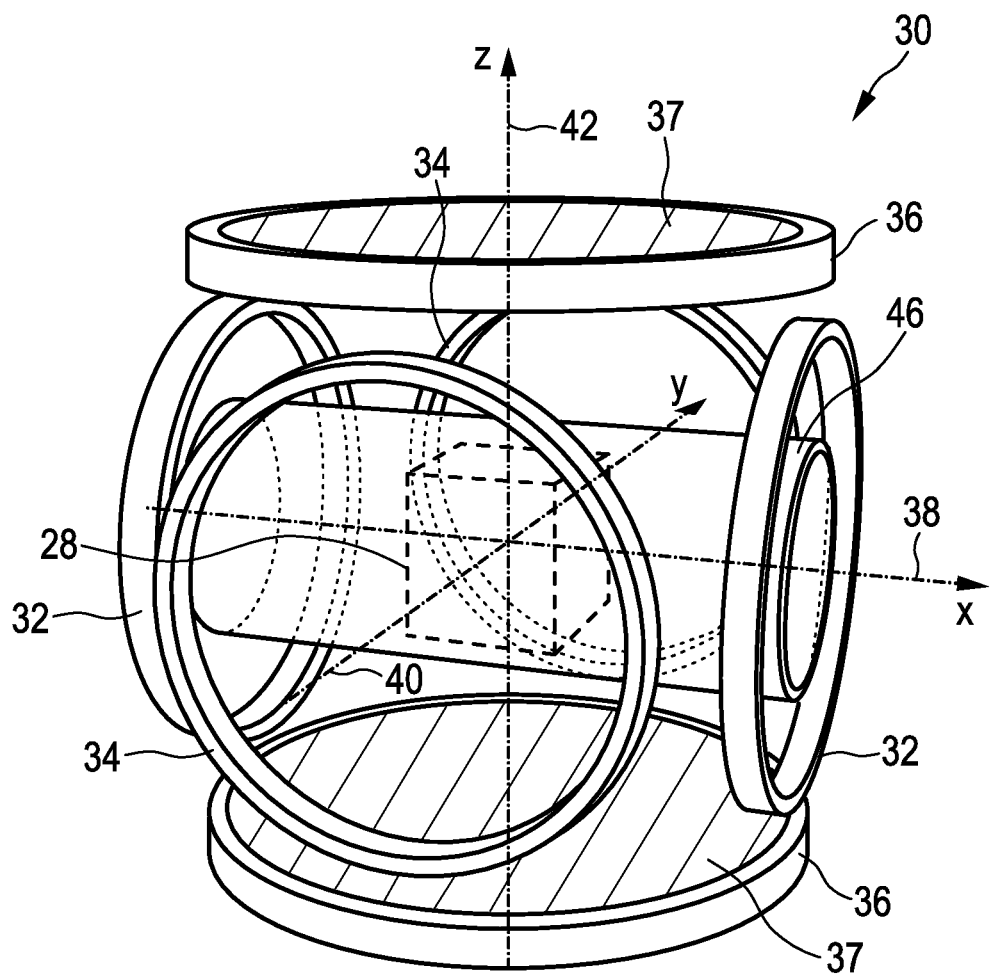
FIG. 3 shows a second embodiment of an MPI apparatus.

Like the first embodiment 10 shown in FIG. 1, the second embodiment 30 of the MPI scanner shown in FIG. 3 has three circular and mutually orthogonal coil pairs 32, 34, 36, but these coil pairs 32, 34, 36 generate the selection field and the focus field only. The z-coils 36, which again generate the selection field, are filled with ferromagnetic material 37. The z-axis 42 of this embodiment 30 is oriented vertically, while the x- and y-axes 38, 40 are oriented horizontally. The bore 46 of the scanner is parallel to the x-axis 38 and, thus, perpendicular to the axis 42 of the selection field. The drive field is generated by a solenoid (not shown) along the x-axis 38 and by pairs of saddle coils (not shown) along the two remaining axes 40, 42. These coils are wound around a tube which forms the bore. The drive field coils also serve as receive coils. The signals picked up by the receive coils are sent through a high-pass filter that suppresses the contribution caused by the applied field.

To give a few typical parameters of such an embodiment: The z-gradient of the selection field, G, has a strength of $G/\mu_0 = 2.5$ T/m, where $\mu_0$ is the vacuum permeability. The selection field generated does either not vary at all over the time or the variation is comparably slow, preferably between approximately 1 Hz and approximately 100 Hz. The temporal frequency spectrum of the drive field is concentrated in a narrow band around 25 kHz (up to approximately 100 kHz). The useful frequency spectrum of the received signals lies between 50 kHz and 1 MHz (eventually up to approximately 10 MHz). The bore has a diameter of 120 mm. The biggest cube 28 that fits into the bore 46 has an edge length of 120 mm/$\sqrt{2} \approx 84$ mm.

As shown in the above embodiments the various magnetic fields can be generated by coils of the same coils pairs and by providing these coils with appropriately generated currents. However, and especially for the purpose of a signal interpretation with a higher signal to noise ratio, it may be advantageous when the temporally constant (or quasi constant) selection field and the temporally variable drive field and focus field are generated by separate coil pairs. Generally, coil pairs of the Helmholtz type can be used for these coils, which are generally known, e.g. from the field of magnetic resonance apparatus with open magnets (open MRI) in which a radio frequency (RF) coil pair is situated above and below the region of interest, said RF coil pair being capable of generating a temporally variable magnetic field. Therefore, the construction of such coils need not be further elaborated herein.

In an alternative embodiment for the generation of the selection field, permanent magnets (not shown) can be used. In the space between two poles of such (opposing) permanent magnets (not shown) there is formed a magnetic field which is similar to that shown in FIG. 2, that is, when the opposing poles have the same polarity. In another alternative embodiment, the selection field can be generated by a mixture of at least one permanent magnet and at least one coil.

The MPI apparatus explained above uses a field-free point (FFP) for spatial incurring. The apparatus according to the present invention that will be explained in the following provides, when applied in an MPI apparatus, the same functionality, but additionally is also able to use a field-free line (FFL) instead for spatial incurring, which considerably improves their sensitivity of the magnetic particle imaging method.

Figure 4:
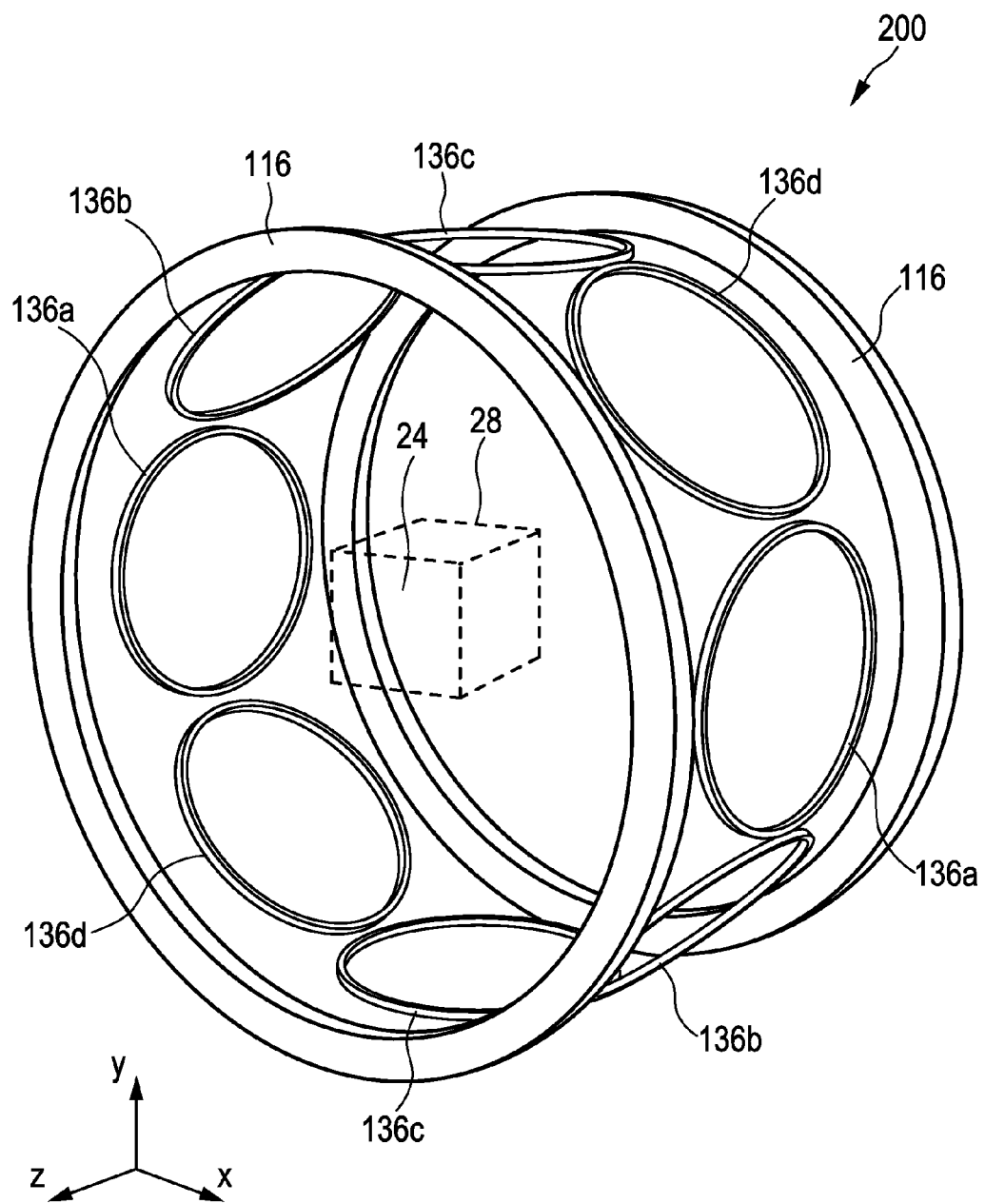
FIG. 4 shows an embodiment of coil assembly for generating and changing a magnetic field in a field of view according to the present invention.
Figure 5:
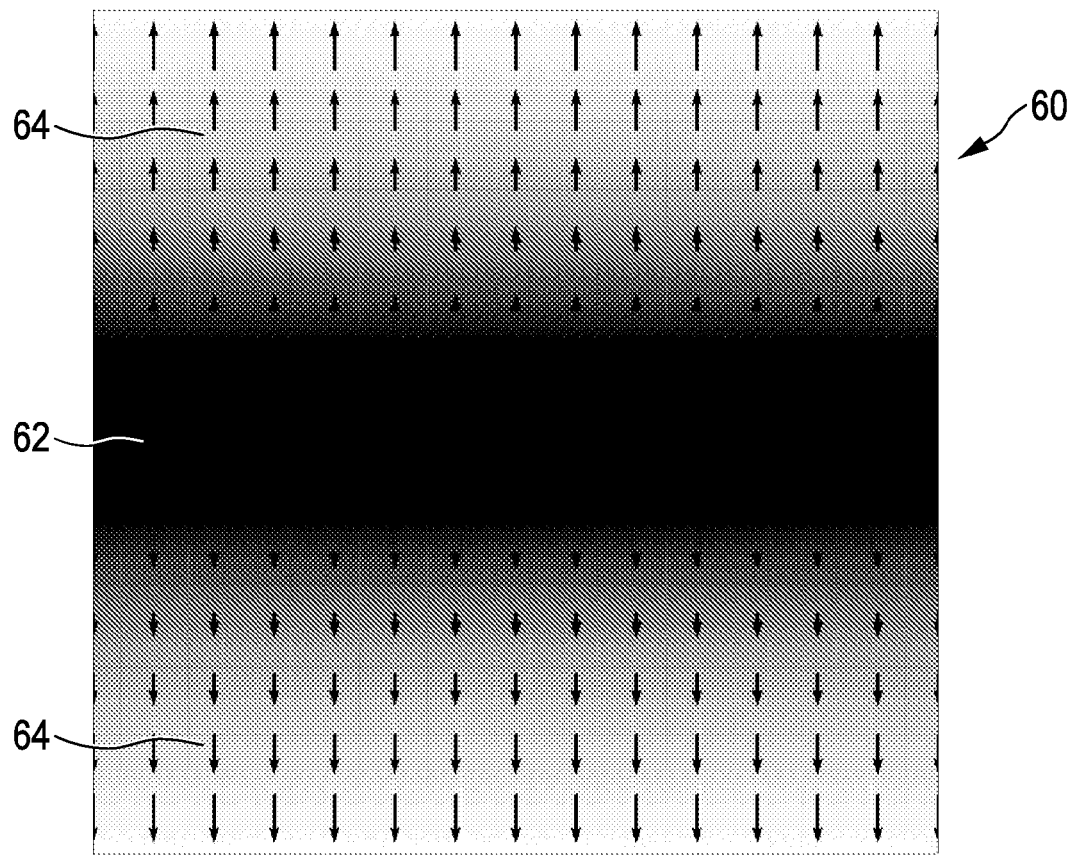
FIG. 5 shows a diagram of a magnetic field having a field free line as generated by the apparatus according to the present invention.

FIG. 4 shows a first embodiment of a coil assembly 200 for generating and changing a magnetic field in a field of view 28. The coil assembly 200 is particularly able to generate and change/move a magnetic field 60 as shown in FIG. 5 in the field of view 28, said magnetic field 60 having a line-shaped first sub-zone 62 having a low magnetic field strength and a second sub-zone 64 having a higher magnetic field strength. For this purpose the embodiment of the coil assembly 200 shown in FIG. 4 comprises four pairs 136a, 136b, 136c, 136d of first coils, which are arranged along a ring around the field of view 28. The two coils of each pair are opposingly arranged on opposite sides of the field of view 28 at equal distance from the isocenter 24 and at equispaced angles along the ring. The centers of all first coils 136 and the isocenter 24 are thus in the same xy-plane. The magnet assembly 200 further comprises one pair 116 of second coils opposingly arranged on opposite sides of the field of view 28 at the open sides of said ring formed by the four pairs 136a-136d of first coils.

For generating current signals for provision to said first and second coils for generating the desired magnetic fields by said first and second coils appropriate generator means (not shown in FIG. 4; see FIG. 8) are provided. Particularly, for each pair, or even better, for each single coil, the generator means is able to generate an individual current as will be explained below.

Still further, control means (also not shown in FIG. 4; see FIG. 8) are provided for controlling said generator means to generate the appropriate current so that the desired magnetic fields are generated by the coils.

A magnetic field 60 having a field free line, i.e. a first sub-zone 62 having a line-shape within a second sub-zone 64, is shown in FIG. 5, as it can be generated and changed/moved by the coil assembly 200 shown in FIG. 4. Here, black indicates zero (low) field strength and white indicates high field strength.

Figure 6:
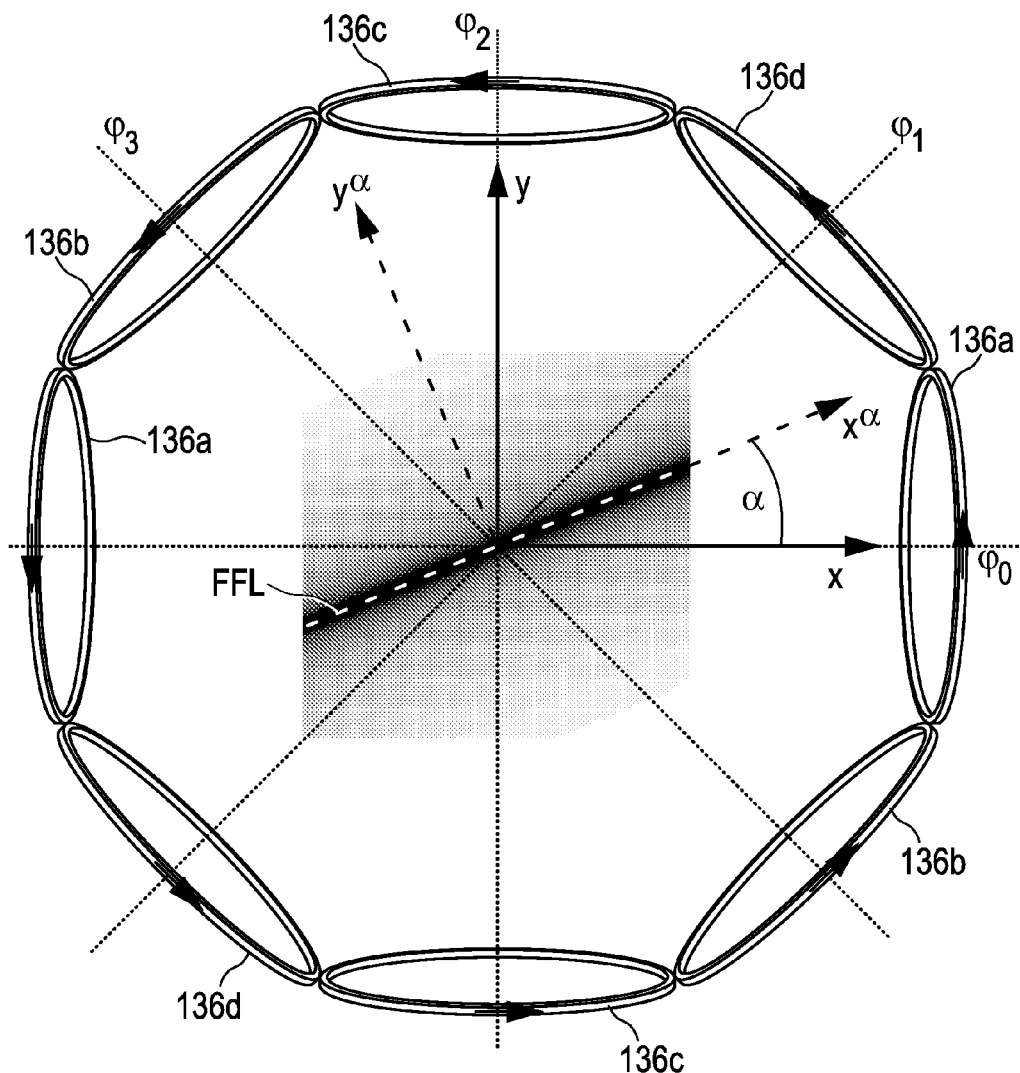
FIG. 6 shows a setup of first coils as used in the first embodiment of the coil assembly shown in FIG. 4.

In FIG. 6 the four pairs 136a-136d of first coils are shown again as positioned on a circle at equispaced angles $N_l = (2\pi/8)l$, $l=0, 1, \ldots, 7$. Every two opposing coils form a Maxwell coil with currents flowing in opposite directions. The continuously rotating FFL can be generated in two ways by such an arrangement.

In a first way, currents $I_l(t) = A(\cos(2 N_l + 2 T) - 3/2)$ are used (A being the AC amplitude), which currents can also be rewritten as $I_l = g_l(\gamma - \cos(2\phi_l - 2\alpha))$ (which are provided to each of the eight coils l of the coil ring. Here, $\phi_l$ is the angular position of the respective first coil l along the ring, $\alpha$ determines the desired direction of the line-shaped first sub-zone in the field of view and $g_l$ and $\gamma$ are predetermined constants. Thus, by varying the parameter $\alpha$ continuously the desired direction of the FFL can be continuously varied over time.

In a second way on the alternating currents $I_l(t) = A \cos(2B_l + 2Tt)$ are used, which currents can also be rewritten as $I_l = g_l \cos(2\phi_l - 2\alpha)$. Additionally, in this mode a DC current is applied to the Maxwell coil pair 116 (see FIG. 4) in z-direction. Preferably, the ratio between the amplitude A of the currents $I_l$ and the DC current $I_m$ provided to the coils m of the second coil pair 116 are chosen in such a way that the Maxwell coil pair 116 in z-direction generates the same gradient as the coil ring of first coils 136 for DC currents $I_f$=−A·3/2.

In the described two modes these coils can thus be regarded as selection field coils for generating a selection field. However, the selection field is no longer static, as in the known MPI apparatus, but is variable over time to move the FFL.

Further, to move the FFL to any position (x, y, z), the coil pair 116 in z-direction, and additionally one coil pair 136a in x-direction and one coil pair 136c in y-direction are additionally used in Helmholtz configuration by superimposing currents flowing in the same direction. By choosing appropriate currents, the FFL can be moved along any predefined trajectory. For instance, the FFL can be moved back and forth perpendicularly to the FFL direction in the xy-plane, while the FFL is rotated slowly with frequency T. Additionally, the FFL is moved along the z-axis for 3D imaging, when the coil assembly 200 is used in an MPI apparatus for MPI imaging. The coils used in Helmholtz configuration can thus be considered as the drive field coils in conventional MPI imaging for generating a magnetic drive field, which is generally a homogenous field which is varied over time.

Figure 7:
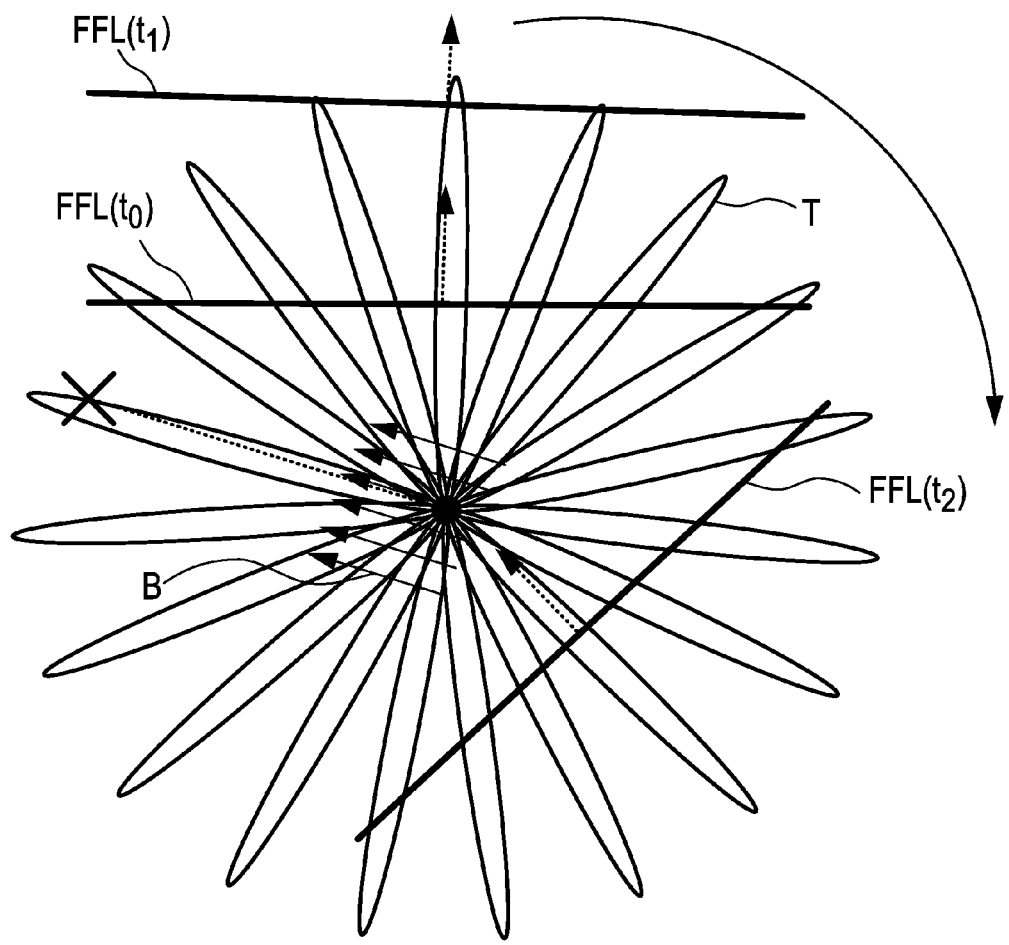
FIG. 7 shows an example of a trajectory for movement a field free line according to the present invention.

An example of a trajectory T for moving the FFL is illustrated in FIG. 7. The rosette illustrates the vector of the drive field as a function of time. At the time $t_x$ the rosette has evolved to the "position" x, and the homogeneous drive field B (sketched in the center) has the direction of the connecting line between the center of the rosette and the position x. The field strength is proportional to the length of this line. Superimposing the selection field and the drive field, the FFL moves along the drive field vector provided that the orientation of the FFL is always perpendicular to the drive field vector. Hence, the FFL scans back and forth while rotating slowly. This is sketched for three arbitrary times $t_0$, $t_1$ and $t_2$.

Figure 8:
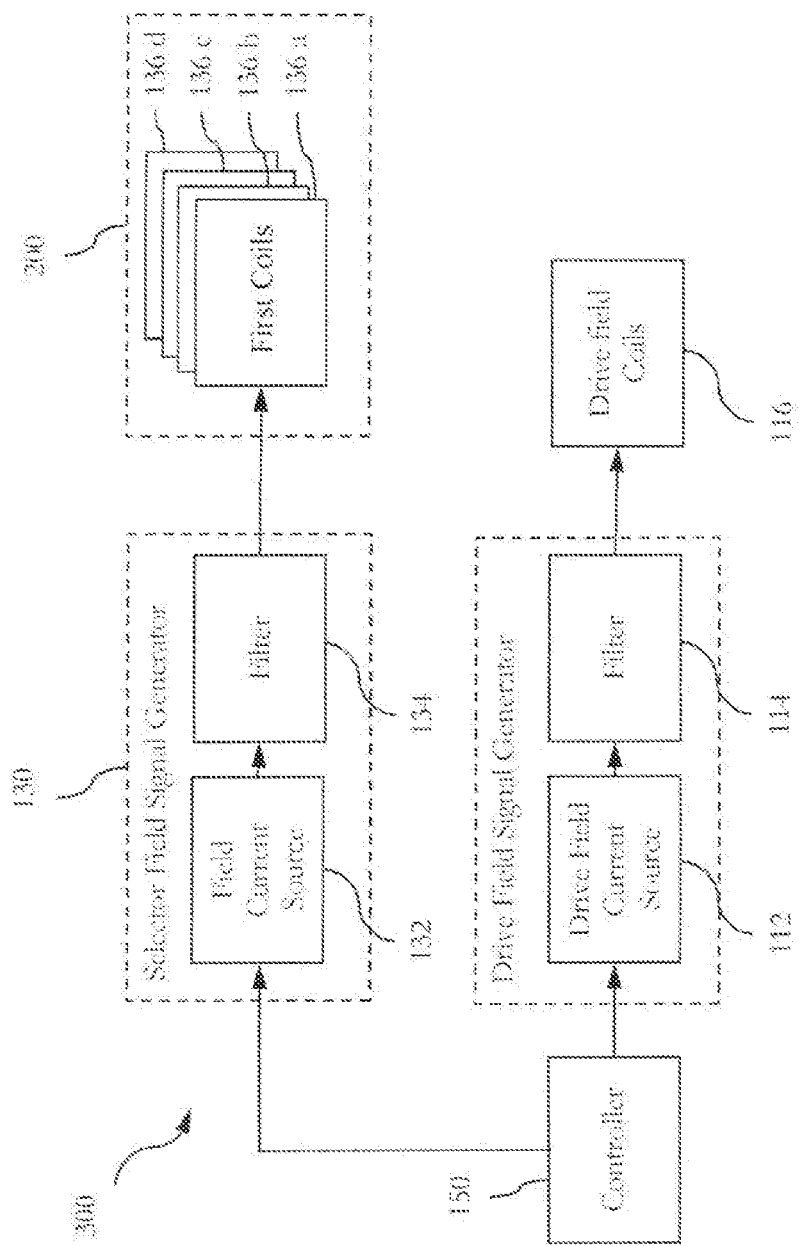
FIG. 8 shows a block diagram of an apparatus for generating and changing a magnetic field in a field of view according to the present invention.

FIG. 8 shows a block diagram of an apparatus 300 for generating and changing a magnetic field in a field of view according to the present invention. The apparatus 300 comprises a coil assembly 200 as illustrated in FIG. 4.

Thus, as explained above, for generating the magnetic (gradient) selection field, selection means are provided comprising a set of selection field (SF) coils 136, preferably comprising at least three pairs of coil elements (first coils). In the embodiment shown here four pairs 136a-136d of selection coils are provided. The selection means further comprises a selection field signal generator unit 130. Preferably, a separate generator subunit is provided for each coil element (or each pair of coil elements) of the set 136 of selection field coils. Said selection field signal generator unit 130 comprises a controllable selection field current source 132 (generally including an amplifier) and a filter unit 134 which provide the respective section field coil element with the selection field current to individually set the gradient strength of the selection field in the desired direction.

The selection field signal generator unit 130 is controlled by a control unit 150, which preferably controls the selection field current generation 130 such that the sum of the field strength and the sum of the gradient strength of all spatial fractions of the selection field is maintained at a predefined level.

For generation of the magnetic drive field the apparatus 100 further comprises drive means comprising a subset of drive field (DF) coils, in this embodiment comprising one pair 116 of oppositely arranged drive field coil elements. The drive field coils are controlled by a drive field signal generator unit 110, preferably comprising a separate drive field signal generation subunit for each coil element (or at least each pair of coil elements) of said set of drive field coils. Said drive field signal generator unit 110 comprises a drive field current source 112 (preferably including a current amplifier) and a filter unit 114 for providing a drive field current to the respective drive field coil. The drive field current source 112 is adapted for generating an AC current and is also controlled by the control unit 150.

By such an apparatus 300 a magnetic field having a field-free line can be generated and moved through a field of view. This can be exploited in various applications. For instance, when used in an MPI apparatus it improves the sensitivity of the MPI method by a factor of more than 10. Compared to the apparatus as shown in the above-cited paper "Magnetic Particle Imaging Using a Field-free Line" of Weizenecker et al. This apparatus consumes about 1000 times less power, which is about the same as a conventional MPI apparatus. Further, it is not limited to 2D imaging, and all static currents can be consolidated on an additional Maxwell coil oriented in z-direction, which is easier to realize and more efficient. Still further, the FFL is of better quality than the FFL produced by the apparatus as shown in said article. In particular, the magnetic field perpendicular to the FFL increases more linear than with the apparatus disclosed in said paper.

Additionally, the apparatus according to the present invention can also be used for generating a field-free point rather than a field-free line, as conventionally used in an MPI apparatus. In this case, only the coil pairs on the x-, y-, and z-axis are used. The z-coil pair is then driven by static current (Maxwell configuration) while all three coil pairs are additionally driven by oscillating currents (Helmholtz configuration) to drive the FFP at any predefined trajectory as generally used in an MPI apparatus.

The currents provided to the drive field coils are generally not fixed. Like in the MPI method driving an FFP along the trajectory, in the FFL mode different trajectories can be used. A preferred trajectory is a radial trajectory (rotating the FFL) which allows to apply a coding scheme which is usually used in CT (e.g. a radon transformation).

Figure 9:
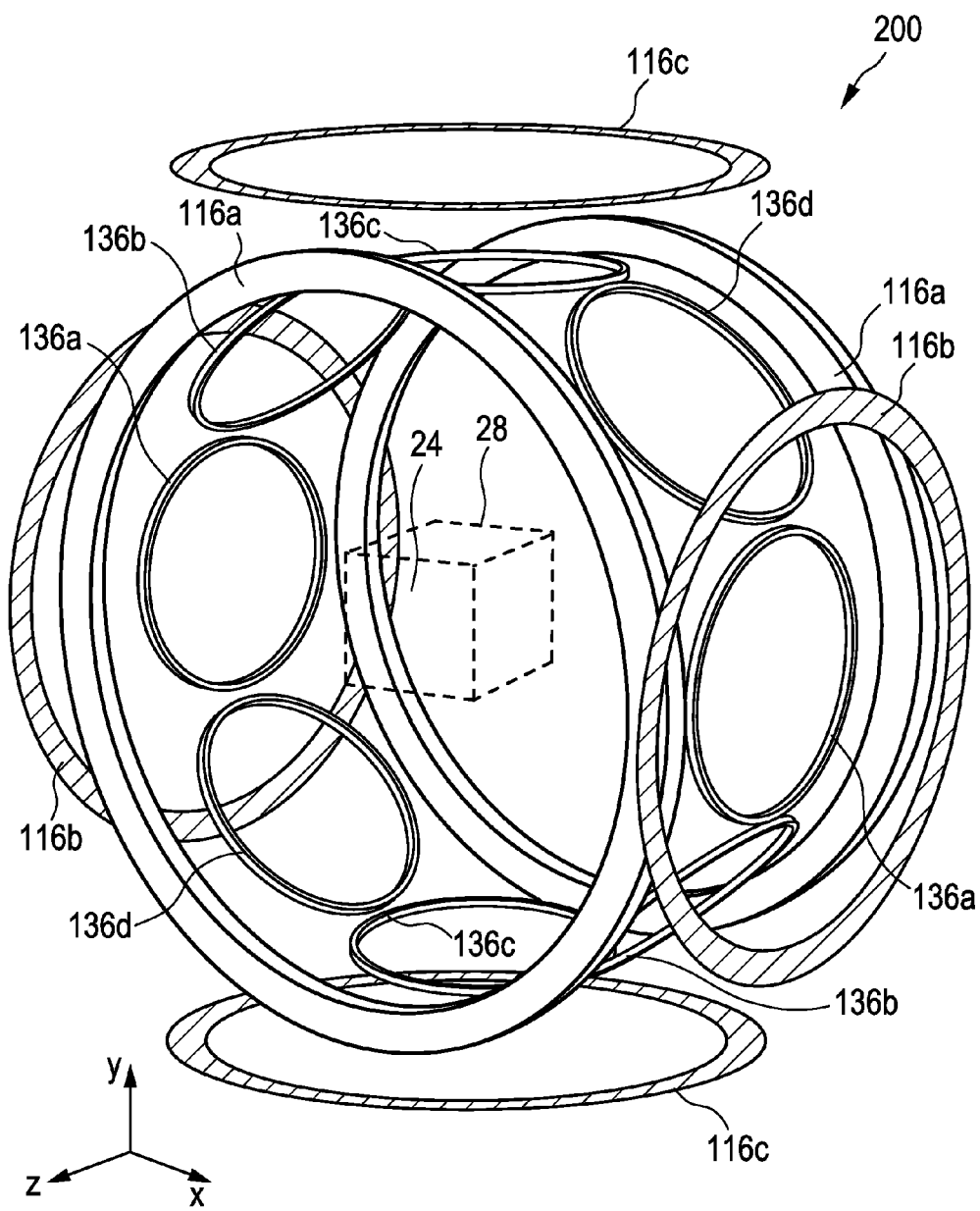
FIG. 9 shows an embodiment of coil assembly according to the present invention for use in a new MPI apparatus.

FIG. 9 illustrates another embodiment of a coil assembly 200 according to the present invention. In addition to the coils shown in the embodiment illustrated in FIG. 4 two further coil pairs 116b, 116c are added so that there is a separate coil pair 116a, 116b, 116c for each direction in space for generating the magnetic drive fields. In this case, preferably the eight coils 136 arranged along the ring are only used for generating the selection field.

Figure 10:
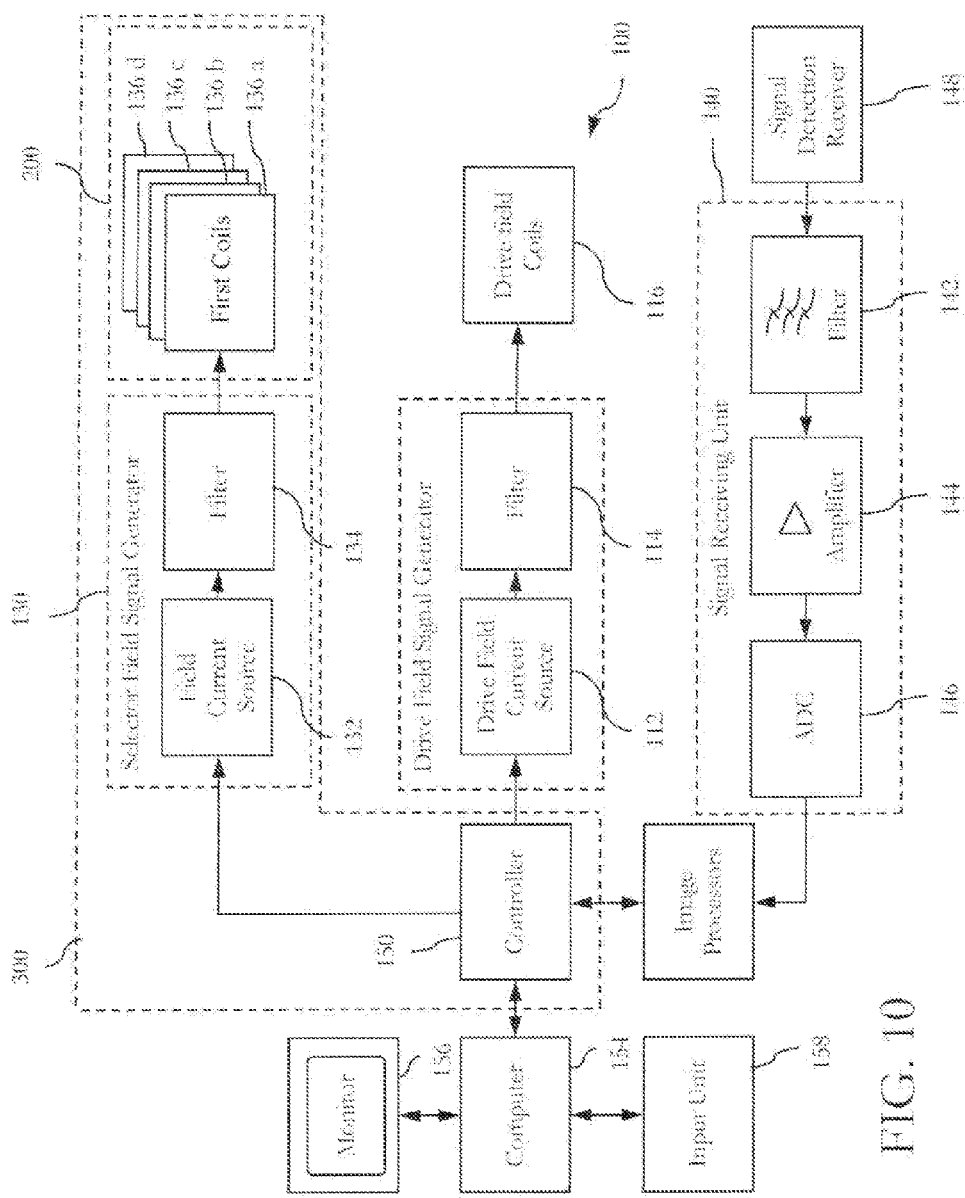
FIG. 10 shows a block diagram of an MPI apparatus according to the present invention.

FIG. 10 shows a general block diagram of an MPI apparatus 100 according to the present invention. The general principles of magnetic particle imaging explained above are valid and applicable to this embodiment as well, unless otherwise specified.

The embodiment of the apparatus 100 shown in FIG. 9 comprises a set of various coils for generating the desired magnetic fields. In particular, it comprises an apparatus 300 for generating and moving a magnetic field as illustrated in FIG. 8. Only the additional elements will be explained in the following.

For signal detection receiving means 148, in particular a receiving coil, and a signal receiving unit 140, which receives signals detected by said receiving means 148, are provided. Said signal receiving unit 140 comprises a filter unit 142 for filtering the received detection signals. The aim of this filtering is to separate measured values, which are caused by the magnetization in the examination area which is influenced by the change in position of the two part-regions (52, 54; 62, 64), from other, interfering signals. To this end, the filter unit 142 may be designed, for example, such that signals which have temporal frequencies that are smaller than the temporal frequencies with which the receiving coil 148 is operated, or smaller than twice these temporal frequencies, do not pass the filter unit 142. The signals are then transmitted via an amplifier unit 144 to an analog/digital converter 146 (ADC). The digitalized signals produced by the analog/digital converter 146 are fed to an image processing unit (also called reconstruction means) 152, which reconstructs the spatial distribution of the magnetic particles from these signals and the respective position which the first part-region 52 of the first magnetic field in the examination area assumed during receipt of the respective signal and which the image processing unit 152 obtains from the control unit 150. The reconstructed spatial distribution of the magnetic particles is finally transmitted via the control means 150 to a computer 154, which displays it on a monitor 156. Thus, an image can be displayed showing the distribution of magnetic particles in the field of view of the examination area.

Further, an input unit 158 is provided, for example a keyboard. A user is therefore able to set the desired direction of the highest resolution and in turn receives the respective image of the region of action on the monitor 156. If the critical direction, in which the highest resolution is needed, deviates from the direction set first by the user, the user can still vary the direction manually in order to produce a further image with an improved imaging resolution. This resolution improvement process can also be operated automatically by the control unit 150 and the computer 154. The control unit 150 in this embodiment sets the gradient field in a first direction which is automatically estimated or set as start value by the user. The direction of the gradient field is then varied stepwise until the resolution of the thereby received images, which are compared by the computer 154, is maximal, respectively not improved anymore. The most critical direction can therefore be found respectively adapted automatically in order to receive the highest possible resolution.

Thus, as explained above, an apparatus for generating and changing a magnetic field having a point-shaped or line-shaped first sub-zone having a low (or zero) magnetic field strength and a second sub-zone having a higher magnetic field strength are provided by the present invention. Such an apparatus can preferably be applied in an MPI apparatus. A magnetic field-free line can be established in an arbitrary direction in a 2D plane by superposition of only three rotated gradient fields. The optimal coil pair numbers to be arranged in the ring around the field of view was found to be three or four depending on whether it is the power loss or the quality of the generated magnetic field which should be optimized. A drastically reduced power consumption compared to the coil assembly proposed by Weizenecker et al. denotes a major step for the feasibility of this arrangement and, due to the improved sensitivity, for MPI in general. The concept of using a field-free line in a magnetic field is, however, not tied to MPI and will find its application in other fields as well.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measured cannot be used to advantage.

Any reference signs in the claims should not be construed as limiting the scope.

The invention claimed is:

1. An apparatus for generating and changing a magnetic field in a field of view (28), said magnetic field having a ball-shaped or line-shaped, first sub-zone (62) having a low magnetic field strength and a second sub-zone (64) having a higher magnetic field strength, which apparatus comprises:
   at least three pairs of first coils (136a-136d), wherein the coils are arranged along a ring around the field of view and wherein the two coils of each pair are opposingly arranged on opposite sides of the field of view,
   at least one pair of second coils (116) opposingly arranged on opposite sides of the field of view at the open sides of said ring,
   generator means (110, 130) for generating current signals for provision to said first and second coils for generating magnetic fields by said first and second coils, and
   control means (150) for controlling said generator means to generate
   i) selection field current signals for provision to said first coils (136a-136d) so that the at least three pairs of first coils generate a gradient magnetic selection field having a pattern in space of its magnetic field strength such that the ball-shaped or line-shaped, first sub-zone having a low magnetic field strength and the second sub-zone having a higher magnetic field strength are formed in the field of view and
   ii) drive field current signals for provision to said second coils (116) and to two pairs (136a, 136c) of first coils so that the at least one pair of second coils and said two pairs of first coils generate a homogeneous magnetic drive field for changing the position in space of the first and second sub-zones in the field of view.

2. An apparatus as claimed in claim 1,
   wherein the control means (150) are adapted for controlling said generator means (110, 130) to generate selection field current signals also for provision to said second coils (116) for contributing to the generation of the magnetic selection field.

3. An apparatus as claimed in claim 1,
   further comprising at least a fourth pair of first coils, wherein all first coils are arranged along a ring around the field of view.

4. An apparatus as claimed in claim 1,
   wherein said first coils (136a-136d) are arranged along said ring without overlapping each other, at equispaced angles and/or at equal distance from the center of the field of view.

5. An apparatus as claimed in claim 1,
   wherein said generator means comprises a selection field current signal generator unit (130) for generating individual selection field current signals for each of said first coils (136a-136d) in the form of a sinusoidal function depending on the angular position of the respective first coil along the ring and the desired direction of a line-shaped first sub-zone.

6. An apparatus as claimed in claim 5,
   wherein said selection field current signal generator unit (130) is adapted for generating said individual selection field current signals $I_l$ for each of said first coils l in the form of $I_l = g_l(\gamma - \cos(2\phi_l - 2\alpha))$, wherein $\phi_l$ is the angular position of the respective first coil l along the ring, a determines the desired direction of the line-shaped first sub-zone in the field of view and $g_l$ and $\gamma$ are predetermined constants.

7. An apparatus as claimed in claim 5,
wherein said selection field current signal generator unit (130) is adapted for generating
said individual selection field current signals $I_l$ for each of said first coils l in the form of $I_l=g_l \cos(2\phi_l-2\alpha)$, wherein $\phi_l$ is the angular position of the respective first coil l along the ring, $\alpha$ determines the desired direction of a line-shaped first sub-zone in the field of view and $g_l$ is a predetermined constant, and
said individual selection field current signals $I_m$ for each of said second coils m for generating a gradient magnetic field in a direction perpendicular to the ring of said first coils.

8. An apparatus as claimed in claim 5,
wherein said selection field current signal generator unit (130) is adapted for generating said individual selection field current signals such that the parameter $\alpha$ determining the desired direction of the line-shaped first sub-zone is continuously varied over time t, in particular according to $\alpha=2\pi ft$, wherein f is the frequency by which the line-shaped first subzone is rotating.

9. An apparatus as claimed in claim 1,
wherein said generator means comprises a drive field current signal generator unit (110) for generating individual drive field current signals for each of said second coils (116) and said two pairs (136a, 136c) of first coils, to which said drive field current signals are provided, causing said first and second coils to generate homogeneous magnet fields having magnetic field vector pointing into the direction of desired movement of the line-shaped first sub-zone, in particular pointing into the direction perpendicular to the line-shaped first sub-zone.

10. An apparatus as claimed in claim 1,
comprising three pairs of second coils (116a, 116b, 116c) opposingly arranged on various opposite sides of the field of view.

11. A magnetic particle imaging apparatus (100) for influencing and/or detecting magnetic particles in a field of view (28), which apparatus comprises an apparatus for generating and changing a magnetic field in the field of view as claimed in claim 1.

12. A magnetic particle imaging apparatus (100) as claimed in claim 11, further comprising:
receiving means comprising at least one signal receiving unit (140) and at least one receiving coil (148) for acquiring detection signals, which detection signals depend on the magnetization in the field of view (28), which magnetization is influenced by the change in the position in space of the first and second sub-zone (52, 54), and
processing means (152) for processing said detection signals.

13. A method for generating and changing a magnetic field in a field of view (28), said magnetic field having a ball-shaped or line-shaped, first sub-zone (62) having a low magnetic field strength and a second sub-zone (64) having a higher magnetic field strength, using at least three pairs of first coils (136a-136d), wherein the coils are arranged along a ring around the field of view and wherein the two coils of each pair are opposingly arranged on opposite sides of the field of view, and at least one pair of second coils (116) opposingly arranged on opposite sides of the field of view at the open sides of said ring, which method comprises the steps of:
generating current signals for provision to said first and second coils for generating magnetic fields by said first and second coils, and
controlling said step of generating current signals to generate
i) selection field current signals for provision to said first coils so that the at least three pairs of first coils generate a gradient magnetic selection field having a pattern in space of its magnetic field strength such that the ball-shaped or line-shaped, first sub-zone having a low magnetic field strength and the second sub-zone having a higher magnetic field strength are formed in the field of view and
ii) drive field current signals for provision to said second coils and to two pairs of first coils so that the at least one pair of second coils and said two pairs of first coils generate a homogeneous magnetic drive field for changing the position in space of the first and second sub-zones sub-zones in the field of view.

14. Computer program storage device comprising a non-transitory computer readable medium with program code means encoded thereon for causing a computer to control an apparatus to perform the method of claim 13 when said computer program is carried out on a computer.

* * * * *